United States Patent

Stokbroekx et al.

(10) Patent No.: US 8,426,434 B2
(45) Date of Patent: Apr. 23, 2013

(54) CRYSTALLINE FORM OF 4-[[4-[[4-(2-CYANOETHENYL)-2,6-DIMETHYL-PHENYL]-AMINO]-2-PYRIMIDINYL]AMINO]BENZONITRILE

(75) Inventors: Sigrid Carl Maria Stokbroekx, Beerse (BE); Carina Leys, Stabroek (BE); Elisabeth Maria Hélène Egide Ghislaine Theunissen, Wilsele (BE); Lieven Elvire Colette Baert, Bruges (BE)

(73) Assignee: Tibotec Pharmaceuticals Ltd., County Cork (IE)

( * ) Notice: Subject to any disclaimer, the term of this patent is extended or adjusted under 35 U.S.C. 154(b) by 333 days.

(21) Appl. No.: 12/668,079

(22) PCT Filed: Jul. 11, 2008

(86) PCT No.: PCT/EP2008/059054
§ 371 (c)(1),
(2), (4) Date: Jan. 7, 2010

(87) PCT Pub. No.: WO2009/007441
PCT Pub. Date: Jan. 15, 2009

(65) Prior Publication Data
US 2010/0189796 A1  Jul. 29, 2010

(30) Foreign Application Priority Data

Jul. 12, 2007 (EP) .................................. 07112392

(51) Int. Cl.
*C07D 239/48* (2006.01)
*A61K 31/505* (2006.01)
(52) U.S. Cl.
USPC .......................................... 514/275; 544/323
(58) Field of Classification Search .................. 544/323; 514/275
See application file for complete search history.

(56) References Cited

FOREIGN PATENT DOCUMENTS

| EP | 0 499 299 B1 | 8/2000 |
|---|---|---|
| WO | WO 03/016306 A1 | 2/2003 |
| WO | WO 2004/016581 A1 | 2/2004 |
| WO | WO 2004/046143 A1 | 6/2004 |
| WO | WO 2006/024668 A1 | 3/2006 |

OTHER PUBLICATIONS

Marcus et al., PubMed Abstract (Intervirology 45(4-6):260-6), 2002.*
Van Heeswijk et al., PubMed Abstract (Antivir Ther. 6(4):201-29) Dec. 2001.*
Janssen, Paul A.J., et al, "In Search of a Novel Anti-HIV Drug: Multidisciplinary Coordination in the Discovery of 4-[[4-[[4-[(1E)-2-Cyanoethenyl]-2,6-dimethylphenyl]amino]-2-pyrimidinyl]amino]benzonitrile (R278474, Rilpivirine)", J. Med. Chem, 2005, pp. 1901-1909, vol. 48, issue 6, American Chemical Society.
Guillemont, Jerome, et al. "Synthesis of Novel Diarylpyrimidine Analogues and Their Antiviral Activity against Human Immunodeficiency Virus Type 1", J. Med. Chem, 2005, pp. 2072-2079, vol. 48, issue 6, American Chemical Society.
International Search Report PCT/EP2008/059054, mailed Feb. 24, 2009.
Bryn, S.R. "Solid-State Pharmaceutical Chemistry", *Chemistry of Materials (Chem Mater)*, vol. 6, pp. 1148-1158, published by American Chemical Society. ( 1994).
Brittain, H.G. "Polymorphism in Pharmaceutical Solids" Guillory, J.K. (1999) Chapter 5 entitled, *Generation of Polymorphs, Hydrates, Solvates and Amorphous Solids*, pp. 183-226. Marcel Dekker, Inc.
Brittain, H.G. "Polymorphism in Pharmaceutical Solids" Grant, David J.W. (1999) Chapter 1 entitled, *Theory and Origin of Polmorphism Solids*, pp. 1-10. Marcel Dekker, Inc.

* cited by examiner

*Primary Examiner* — Deepak Rao
(74) *Attorney, Agent, or Firm* — Rajiv S. Shah (57) ABSTRACT

This invention concerns polymorph I of TMC278, its use and preparation. It further concerns pharmaceutical formulations comprising this polymorph.

12 Claims, 8 Drawing Sheets

Figure 2: Powder XRD pattern of TMC278 polymorph I.

Figure 3: Differential scanning calorimetry (DSC): TMC278 polymorph I.

Figure 4: Dissolution Plot of TMC278 polymorph I.

Figure 6: Powder XRD pattern of TMC278 polymorph II.

Figure 7: Differential scanning calorimetry (DSC): TMC278 polymorph II.

Figure 8: Dissolution Plot of TMC278 polymorph II.

CRYSTALLINE FORM OF 4-[[4-[[4-(2-CYANOETHENYL)-2,6-DIMETHYL-PHENYL]-AMINO]-2-PYRIMIDINYL] AMINO]BENZONITRILE

CROSS REFERENCE TO RELATED APPLICATIONS

This application is a national stage of PCT Application No. PCT/EP2008/059054, filed 11 Jul. 2008, which claims priority for European Patent Application No. 07112392.1, filed 12 Jul. 2007, all of which are hereby incorporated by reference in their entirety.

FIELD OF THE INVENTION

This invention concerns a crystalline form of TMC278, its use and preparation. It further concerns pharmaceutical formulations comprising this crystalline form.

BACKGROUND OF THE INVENTION

The treatment of Human Immunodeficiency Virus (HIV) infection, known as cause of the acquired immunodeficiency syndrome (AIDS), remains a major medical challenge. Currently available drug therapies include nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors (PIs), fusion inhibitors and the more recent CCR5 and integrase inhibitors.

Although effective in suppressing HIV, each of these drugs, when used alone, is confronted with the emergence of resistant mutants. This led to the introduction of combination therapy of several anti-HIV agents usually having a different activity profile. In particular the introduction of "HAART" (Highly Active Anti-Retroviral Therapy) resulted in a remarkable improvement in anti-HIV therapy, leading to a dramatic reduction in HIV-associated morbity and mortality. However, none of the currently available combination therapies can completely eradicate HIV. Even HAART can face the emergence of resistance, often due to non-compliance with the prescribed therapy. In these cases HAART can be made effective again by replacing one of its components by one of another class. If applied correctly, HAART combinations can suppress the virus for many years, up to decades, to a level where it no longer can cause the outbreak of AIDS.

One class of HIV drugs often used in HAART is that of the NNRTIs, a number of which are currently on the market and several others are in various stages of development. An NNRTI currently in development is the compound 4-[[4-[[4-(2-cyanoethenyl)-2,6-dimethylphenyl]-amino]-2-pyrimidinyl]-amino-]-benzonitrile, generically designated as rilpivirine, also known as R278474 or TMC278. This compound not only shows pronounced activity against wild type HIV, but also against many of its mutated variants. The compound TMC278, its pharmacological activity as well as a number of procedures for its preparation have been described in WO 03/16306. The TMC278 described in this reference is in crystalline form and this form will hereinafter be referred to as "Polymorph II" of TMC278. The present invention concerns another polymorphic form of TMC278, which hereinafter will be referred to as "Polymorph I" of TMC278. Polymorph I of TMC278 has previously not been described and is a crystalline form that possesses beneficial properties as will be outlined hereinafter.

Next to activity, the pharmacokinetic profile plays an important role in the effectiveness of any given drug. This in turn coincides with the drug's bioavailability influencing dosing required to reach a therapeutically effective concentration of the drug in a patient. Drugs with a low bioavailability need to be administered in higher doses, thereby increasing the risk of adverse effects. Higher doses further implicate larger dosage forms or an increase in the frequency of administration, or both. These factors may influence adherence to and concomitant effectiveness of anti-HIV treatment. Inadequate treatment in turn increases the risk of emergence of mutant HIV strains.

TMC278 has a relatively low solubility in water resulting in poor bioavailability. Unexpectedly, it has now been found that a new crystalline form of TMC278 has an increased intrinsic dissolution rate and higher solubility in acidic aqueous media. These properties are beneficial as regards bioavailability making the new crystalline form attractive for application in solid dosage forms, but also in certain liquid dosage forms such as aqueous dispersions. The latter may find use in formulations for parenteral administration.

In addition, the use of a particular polymorphic form of an active ingredient is recommendable because the composition of polymorphic mixtures may vary from batch to batch or may vary in time thereby causing changes in the properties of that active ingredient. If the polymorphic form is not held constant during clinical and stability studies, the exact dosage used or measured may not be comparable from one lot to the next. Once a pharmaceutical compound is produced for human use, it is important to recognize the polymorphic form delivered in each dosage form to assure that the production process uses the same form and that the same amount of drug is included in each dosage. Therefore, it is necessary to assure that either a single polymorphic form or some known combination of polymorphic forms is present.

Currently used anti-HIV drugs require frequent administration of relatively high doses. The number and/or volume of dosage forms that need to be administered are commonly referred to as the "pill burden". A high pill burden causes patients to fail to comply with the prescribed dosage regimen thereby not only reducing the effectiveness of the treatment but also causing the emergence of resistant mutants. Hence there is a need for anti-HIV therapy that avoids a high pill burden, involving the administration of dosage forms of relatively small size not requiring frequent dosing. It would be further desirable to provide anti-HIV therapy that can be administered at long time intervals such as a week, a month, or longer.

Current therapies do not allow to completely eradicate HIV so that individuals infected with HIV pose a continuous risk of infecting others. After initial infection it takes a long time before the outbreak of the first symptoms of AIDS. People may live for years with the infection without experiencing any effects of it thereby being unaware of the risk of further transferring the virus to others. Prevention of HIV transmission therefore is crucial because of the imminent risk of individuals being in contact with HIV infected persons of becoming infected. This in particular is the case for those providing medical care to infected patients such as physicians, nurses or dentists. Another group of individuals at risk are breast-fed infants whose mother is infected or at risk of becoming infected, especially in developing countries where alternatives for breast-feeding are less obvious. Hence there is a need for easy to apply means that provide effective prevention against transmission of HIV. Providing such prevention means is a further object of the present invention.

The crystalline form of TMC278 subject of this invention can be formulated into micro- or nanoparticles that function as depot formulations in the treatment of HIV infection as well as in the prevention of transmission of HIV. Nanoparticles of drug substances are known having been described e.g. in EP-A-0 499 299. It has been found that micro- or nanoparticle formulations of Polymorph I of TMC278 can be administered intermittently at time intervals of one week or longer resulting in plasma levels sufficient to suppress multiplication of HIV. The number of administrations is reduced thereby, which is beneficial in terms of pill burden and drug compliance of the patient. Such micro- or nanoparticle formulations may find use in the long-term treatment or prevention of HIV.

Because of its beneficial properties, Polymorph I of TMC278 is particularly suited for use in micro- or nanoparticle formulations. Such formulations are expected to result in higher blood plasma levels for a given amount of TMC278 administered. Moreover, the desired blood plasma levels will be reached quicker. Relatively high blood plasma levels may be required where high safety margins are desired.

SUMMARY OF THE INVENTION

The present invention concerns a particular crystalline form of TMC278, i.e. polymorph I of (E) 4-[[4-[[4-(2-cyanoethenyl)-2,6-dimethylphenyl]amino]-2-pyrimidinyl]amino]benzonitrile, i.e. of TMC278, also referred to as rilpivirine. This polymorph is characterized by the physicochemical parameters mentioned in the examples.

The invention furthermore concerns a process for preparing this crystalline form. In a further aspect, the invention concerns a solid pharmaceutical composition comprising as active ingredient polymorph I of TMC278, and a pharmaceutically acceptable carrier.

This invention furthermore concerns a micro- or nanoparticle pharmaceutical composition for administration by intramuscular or subcutaneous injection, comprising a therapeutically effective amount of polymorph I of TMC278, in micro- or nanoparticle form, having a surface modifier adsorbed to the surface thereof, suspended in a pharmaceutically acceptable aqueous carrier.

The invention further concerns a method of treating a subject infected with HIV, said method comprising the administration to said subject, by intramuscular or subcutaneous injection, of an anti-HIV effective amount of a micro- or nanoparticle composition as specified herein. In another aspect, the said method is for the long term treatment and the composition is administered or is to be administered intermittently at a time interval that is in the range of one week to one year, or one week to two years, or one month to three months. Or, alternatively, the invention concerns the use of a micro- or nanoparticle composition as specified herein, for the manufacture of a medicament for treating HIV infection. Or, said use is for the long term treatment and the composition is administered or is to be administered intermittently at a time interval that is in the range of one week to one year, or one week to two years, or one month to three months.

The invention further concerns a method for the prevention of HIV infection in a subject at risk of being infected by HIV, said method comprising the administration to said subject, by intramuscular or subcutaneous injection, of an amount effective in preventing HIV infection of a micro- or nanoparticle composition as specified herein. In another aspect, the said method is for the long term treatment and the composition is administered or is to be administered intermittently at a time interval that is in the range of one week to one year, or one week to two years, or one month to three months. Or, alternatively, the invention concerns the use of a micro- or nanoparticle composition as specified herein, for the manufacture of a medicament for the prevention of HIV infection in a subject at risk of being infected by HIV. Or, said use is for the long term treatment and the composition is administered or is to be administered intermittently at a time interval that is in the range of one week to one year, or one week to two years, one month to three months.

Further pharmaceutical compositions, methods of treatment or prevention, as well as uses for the manufacture of medicaments based on these compositions will be described hereinafter and are meant to be part of the present invention.

DESCRIPTION OF THE INVENTION

As used herein, a polymorphic form of a compound refers to the same chemical entity, but in a different crystalline arrangement.

The crystalline form I of TMC278 subject of this invention may also be referred to as "form I of TMC278", "polymorph I of TMC278", or by similar expressions, and is characterized by the physicochemical parameters outlined hereinafter. A second polymorphic form of TMC278 is designated herein as Form II and is the form obtained when synthesizing this compound using the procedures of WO 03/16306. It may be also referred to as "form II of TMC278", "polymorph II of TMC278", or by similar terms.

The chemical structure of TMC278 can be represented by formula:

(I)

TMC278 exists in two stereochemical configurations at the double bond of the cyanoethenyl moiety, i.e. the E (Entgegen) configuration (E-isomer) and the Z (Zusammen) configuration (Z-isomer). Unless otherwise mentioned, the term TMC278, or similar terms, refers to the E-isomer, in particular the E-isomer substantially free of the Z-isomer. Whenever reference is made herein to the E-isomer, the pure E-isomer or any isomeric mixture of the E- and the Z-isomers wherein the E-isomer is predominantly present is meant, i.e. an isomeric mixture containing more than 70% or in particular more than 80% of the E-isomer, more in particular more than 90% of the E-isomer. Of particular interest is the E-isomer substantially free of the Z-isomer. Substantially free in this context refers to E-Z-mixtures with no or almost no Z-isomer, e.g. isomeric mixtures containing as much as 90%, in particular 95% or even 98% or 99% of the E-isomer.

TMC278 is an HIV inhibitor, in particular of HIV-1, the aetiological agent of the Acquired Immune Deficiency Syndrome (AIDS) in humans. TMC278 shows activity against drug and multidrug resistant HIV strains, in particular activity against HIV strains that have acquired resistance to one or more non-nucleoside reverse transcriptase inhibitors, in particular efavirenz, nevirapine and delavirdine. TMC278 may find use in the treatment of other conditions associated with HIV infection include thrombocytopaenia, Kaposi's sarcoma and infection of the central nervous system characterized by progressive demyelination, resulting in dementia and symptoms such as, progressive dysarthria, ataxia and disorientation, peripheral neuropathy, progressive generalized lymphadenopathy (PGL), and AIDS-related complex (ARC).

Polymorph I of TMC278, subject of this invention, is useful in the treatment of individuals infected by HIV and in the prophylaxis of HIV infection. It may also be used in the treatment and prevention of the above referred conditions associated with HIV. The invention therefore also concerns a method of treating HIV infection in humans, or a method of preventing HIV infection in humans, which comprises administering to a human in need thereof a therapeutically effective amount of polymorph I of TMC278. Alternatively, the invention concerns a method of treating diseases associated with HIV infection in humans, which comprises administering to a human in need thereof a therapeutically effective amount of polymorph I of TMC278.

Compared to Polymorph II, Polymorph I of TMC278 shows increased solubility at lower pH and increased intrinsic dissolution rates. Given the poor solubility of TMC278, these properties will act beneficially on bioavailability so that effective blood plasma levels are more easily obtained, making the active ingredient better available to exert its antiviral action. Polymorph I of TMC278 therefore will be better resorbed in more acidic media such as in gastric juice.

Polymorph I of TMC278 can be prepared by dissolving TMC278 in a ketone solvent, such as a $diC_{1-4}$alkyl ketone, e.g. 2-butanone, methyl isopropyl ketone, methyl isobutyl ketone, 2-pentanone, 3-pentanone, and in particular in acetone, which is heated to reflux temperature, and allowing this solution to cool, in particular below 0° C. Upon removal of the solvent crystals are obtained, which can be dried. The starting material TMC278 can be prepared as described in WO 03/16306. the term $C_{1-4}$alkyl refers to a straight or branched saturated hydrocarbon of one to four carbon atoms.

The present invention also relates to a solid pharmaceutical composition comprising a pharmaceutically acceptable carrier and as active ingredient a therapeutically effective amount of polymorph I of TMC278. The composition may be in the form of a solid dosage form such as a tablet or capsule, or a suspension. The pharmaceutical compositions of the invention can be prepared by combining an effective amount of the polymorph I of TMC278 as the active ingredient in intimate admixture with a pharmaceutically acceptable carrier. The pharmaceutical compositions preferably are formulated into unit dosage forms suitable for oral administration such as tablets and capsules. The carrier may comprise any of the usual pharmaceutical media such as, for example, wetting agents, fillers, diluents, glidants, binders, disintegrants, lubricants, and optional excipients such as flavors, sweeteners and colors. Tablets may optionally be film-coated. Injectable suspensions may also be prepared in which case appropriate liquid carriers, suspending agents and the like may be employed.

The pharmaceutical compositions in unit dose form may contain polymorph I of TMC278 in a quantity that is in the range of from about 5 to about 500 mg, or from about 10 mg to about 250 mg, or from about 20 mg to about 200 mg, or from about 25 mg to about 150 mg, e.g. about 25 mg, about 50 mg, about 75 mg, about 100 mg or about 150 mg. Of interest is a pharmaceutical composition, as specified herein, comprising:

(a) from 5 to 50% of polymorph I of TMC278;
(b) from 0.01 to 5% of a wetting agent;
(c) from 40 to 92% of a diluent;
(d) from 0 to 10% of a polymer;
(e) from 2 to 10% of a disintegrant;
(f) from 0.1 to 5% of a glidant;
(g) from 0.1 to 1.5% of a lubricant.

Polymorph I of TMC278 can furthermore be converted into micro- or nanoparticle suspensions that can be used in the long-term treatment of HIV infection as well as in the long-term prevention of HIV infection requiring only a limited number of drug administrations. This is beneficial in terms of pill-burden as well as patient compliance with the prescribed dose regimen.

The term "prevention HIV infection" relates to the prevention or avoidance of a subject becoming infected with HIV. The source of infection can be various, such as a material containing HIV, in particular a body fluid that contains HIV such as blood or sperm, or another subject who is infected with HIV. Prevention of HIV infection relates to the prevention of the transmission of the virus from the material containing HIV or from the HIV infected individual to an uninfected person, or relates to the prevention of the virus from entering the body of an uninfected person. Transmission of HIV can be by any known cause of HIV transfer such as by sexual transmission or by contact with blood of an infected subject, e.g. medical staff providing care to infected subjects, when handling blood samples or with blood transfusion. It can also be by contact with infected cells, e.g. when carrying out laboratory experiments with HIV infected cells.

As used herein the term "treatment of HIV infection" relates to the treatment of a subject being infected with HIV. The term "treatment of HIV infection" also relates to the treatment of diseases associated with HIV infection mentioned above. The terms "treatment of HIV infection", "anti-HIV therapy", as well as similar terms, refer to a treatment by which the viral load of HIV (represented as the number of copies of viral RNA in a specified volume of serum) is reduced. The more effective the treatment, the lower the viral load. Preferably the viral load should be reduced to as low levels as possible, e.g. below about 200 copies/ml, in particular below about 100 copies/ml, more in particular below 50 copies/ml, if possible below the detection limit of the virus. Reductions of viral load of one, two or even three orders of magnitude (e.g. a reduction in the order of about 10 to about $10^2$, or more, such as about $10^3$) are an indication of the effectiveness of the treatment. Another parameter to measure effectiveness of anti-HIV treatment is the CD4 count, which in normal adults ranges from 500 to 1500 cells per μl. Lowered CD4 counts are an indication of HIV infection and once below about 200 cells per μl, AIDS may develop. An increase of CD4 count, e.g. with about 50, 100, 200 or more cells per μl, is also an indication of the effectiveness of anti-HIV treatment. The CD4 count in particular should be increased to a level above about 200 cells per μl, or above about 350 cells per μl. Viral load or CD4 count, or both, can be used to diagnose the degree of HIV infection.

The terms "effective treatment of HIV" and similar terms refer to that treatment that lowers the viral load, or increases CD4 count, or both, as described above. The terms "effective prevention of HIV" and similar terms refer to that situation where there is a decrease in the relative number of newly infected subjects in a population in contact with a source of HIV infection such as a material containing HIV, or an HIV infected subject. Effective prevention can be measured, for example, by measuring in a mixed population of HIV infected and non-infected individuals, if there is a decrease of the relative number of newly infected individuals, when comparing non-infected individuals treated with a micro- or nanoparticle composition of the invention, and non-treated non-infected individuals. This decrease can be measured by statistical analysis of the numbers of infected and non-infected individuals in a given population over time.

The terms "therapeutically effective amount", "an amount, effective in preventing HIV infection", and similar terms, refer to amounts of the active ingredient TMC278 that result in efficacious blood plasma levels. With "efficacious blood plasma levels" is meant those blood plasma levels of the HIV inhibitor TMC278 that provide effective treatment or effective prevention of HIV infection. The term "subject" in particular relates to a human.

The term "micro- or nanoparticles" refers to particles in the micrometer or nanometer range. In one embodiment, the micro- or nanoparticle compositions of the invention comprise Polymorph I TMC278 in nanoparticle form. The average effective particle size of the micro- or nanoparticles of the present invention may be below about 50 μm, or below about 20 μm, or below about 10 μm, or below about 1000 nm, or below about 500 nm, or below about 400 nm, or below about 300 nm, or below about 200 nm. The lower limit of the average effective particle size may be low, e.g. as low as about 100 nm or as low as about 50 nm. In one embodiment, the average effective particle size is in the range of about 50 nm to about 50 μm, or about 50 nm to about 20 μm, or about 50 nm to about 10 μm, or about 50 nm to about 1000 nm, about 50 nm to about 500 nm, or about 50 nm to about 300 nm, or about 100 nm to about 250 nm, or about 125 nm to about 175 nm, e.g. about 130 nm, or about 150 nm.

As used herein, the term average effective particle size has its conventional meaning and can be measured by art-known particle size measuring techniques such as, for example, sedimentation field flow fractionation, photon correlation spectroscopy, laser diffraction or disk centrifugation. The average effective particle sizes mentioned herein may be related to volume distributions of the particles. In that instance, by "an effective average particle size of less than about 50 μm" it is meant that at least 50% of the volume of the particles has a particle size of less than the effective average of 50 μm, and the same applies to the other effective particle sizes mentioned. In a similar manner, the average effective particle sizes may be related to weight distributions of the particles but usually this will result in the same or about the same value for the average effective particle size.

The micro- or nanoparticle compositions of polymorph I of TMC278 provide release of the active ingredient TMC278 over a prolonged period of time and therefore they can also be referred to as sustained or delayed release compositions, or as depot formulations. After administration, such compositions stay in the body and steadily release TMC278, keeping the active ingredient in the patient's system for a prolonged period of time, thereby providing anti-HIV treatment or prevention of HIV infection. Once administered, the blood plasma levels of TMC278 are more or less stable, i.e. they fluctuate within limited margins. The blood plasma levels approach more or less a steady state mode or more or less a zero order release rate. In some instances there may be an initial plasma concentration peak after administration.

As used herein with the term "prolonged period of time", there is meant a term (or time period) that may be in the range of one week up to one year or up to two years, or a term in the range of one to two weeks, or two to three weeks, or three to four weeks, or a term in the range of one to two months, or two to three months, or three to four months, or three to six months, or six months to 12 months, or 12 months to 24 months.

The plasma levels of the active ingredient, TMC278, should be above a threshold value. In case of therapeutic application said threshold value is the lowest plasma level at which TMC278 provides effective treatment of HIV infection. In case of prevention of HIV infection said threshold value is the lowest plasma level at which TMC278 is effective in preventing transmission of HIV infection.

With "long term" for example as used in relation to "long term prevention of HIV infection" or "long term treatment of HIV infection", or similar terminology, there are meant terms that may be in the range of one week up to one year or up to two years, or longer, such as five or 10 years. In particular in the case of treatment of HIV infection, such terms will be long, in the order of one to several years. Such terms may also be relatively short, in particular in the case of prevention, e.g. one week up to one year.

The micro- or nanoparticle compositions of polymorph I of TMC278 can be administered at various time intervals. When used in the prevention of HIV infection, the micro- or nanoparticle compositions of this invention can be administered only once or a limited number of times such as twice, three, four, five or six times, or more. This may be recommendable where prevention is required during a limited period of time, such as the period during which there is a risk of infection.

The micro- or nanoparticle compositions of the present invention can be administered at the time intervals mentioned above, such as at a time interval that is in the range of one week to one month, or in the range of one month to three months, or in the range of three months to six months, or in the range of six months to twelve months, e.g. once every two weeks, or once every month, or once every three months. In another embodiment the time interval is in the range of one to two weeks, or two to three weeks, or three to four weeks, or the time interval is in the range of one to two months, or two to three months, or three to four months, or three to six months, or six months to 12 months, or 12 months to 24 months. The time interval may be at least one week, but may also be several weeks, e.g. 2, 3, 4, 5 or 6 weeks, or one month, or 2, 3, 4, 5 or 6 months, or longer, e.g. 9 or 12 months. To further improve compliance, patients can be instructed to take their medication at a certain day of the week, where the composition is administered on a weekly schedule, or at a certain day of the month in case of a monthly schedule.

The length of the time intervals between each administration of a micro- or nanoparticle composition of the invention may vary. For example said time intervals may be selected in function of the blood plasma levels. The intervals may be shorter where the blood plasma levels of TMC278 are deemed too low, or longer where the blood plasma levels of TMC278 are deemed too high. The micro- or nanoparticle compositions of the invention may be administered at equal time intervals, without any interjacent additional administrations. Having time intervals of the same length has the advantage that the administration schedule is simple, e.g. administration takes place at the same day in the week, or the same day in the month.

The dose (or amount) of TMC278 administered, depends on the amount of TMC278 in the micro- or nanoparticle compositions of the invention, or on the amount of a given composition that is administered. Where higher blood plasma levels are desired, either or both of a composition of higher TMC278 concentration, or more of a given composition, may be administered. This applies vice versa if lower plasma levels are desired. Also a combination of varying time intervals and varying dosing may be selected to attain certain desired blood plasma levels. The dose (or amount) of TMC278 administered also depends on the frequency of the administrations (i.e. the time interval between each administration). Usually, the dose will be higher where administrations are less frequent.

The dosing regimen also depends on whether prevention or treatment of HIV infection is envisaged. In case of therapy, the dose of TMC278 administered or the frequency of dosing, or both, are selected so that the blood plasma concentration of TMC278 is kept above a minimum blood plasma level (or $C_{min}$). The latter term refers to the blood plasma level of TMC278 that provides effective treatment of HIV. In particular, the blood plasma level of TMC278 is kept at a level above a minimum blood plasma level of about 10 ng/ml, or above about 13.5 ng/ml, or above about 15 ng/ml, or above about 20 ng/ml, or above about 40 ng/ml, or higher, e.g. above about 50 ng/ml, or above about 90 ng/ml, or above about 270 ng/ml, or above about 540 ng/ml. Or the blood plasma levels of TMC278 may be kept within certain ranges, in particular ranges starting from a minimum blood plasma level selected from those mentioned above and ending at a higher blood plasma levels selected from those mentioned above and selected from 500 ng/ml and 1000 ng/ml, e.g. from about 10 to about 20, from about 20 to about 90, from 90 to 270, from 270 to 540, from 540 to 1000, each time from about the indicated value in ng/ml to about the indicated value in ng/ml.

In the instance of HIV prevention, the term "minimum blood plasma level" (or $C_{min}$) refers to the lowest blood plasma level of TMC278 that provides effective prevention of HIV infection. For HIV prevention, the blood plasma level of TMC278 can be kept at a level above a minimum blood plasma level mentioned above in relation to therapy, or can be kept at a lower level, e.g. at a level above about 4 ng/ml, or about 5 ng/ml, or about 8 ng/ml. Plasma levels of TMC278 may be kept at somewhat higher levels to have a safety margin. Such higher levels start from about 50 ng/ml or more. The blood plasma level of TMC278 can be kept at a level that is in the ranges mentioned above in relation to therapy, but where the lower limits include the blood plasma levels of about 4 ng/ml, or about 5 ng/ml, or about 8 ng/ml.

An advantage of TMC278 is that it can be used up to relatively high blood plasma levels without any significant side effects. The maximum plasma concentrations of TMC278 ($C_{max}$) may reach relatively high levels, even up to about 500 ng/ml or about 1000 ng/ml. In an embodiment, the amount and the frequency of administrations of TMC278 to be administered are selected such that the blood plasma concentrations are kept during a long term at a level comprised between a maximum plasma level (or $C_{max}$ as specified above) and a minimum blood plasma level (or $C_{min}$ as specified above).

In certain instances it may be desirable to keep the plasma levels of TMC278 at relatively low levels, e.g. as close as possible to the minimum blood plasma levels specified herein. This will allow reducing the frequency of the administrations and/or the quantity of TMC278 administered with each administration. The plasma levels of TMC278 may be kept at relatively low levels in the instance of prevention. In other instances it may be desirable to keep the plasma levels of TMC278 at relatively higher levels, e.g. the minimum blood plasma level may be equal to the lowest blood plasma level of TMC278 that provides effective treatment of HIV, such as the specific levels mentioned herein.

In the instance of prevention, the dose to be administered should be calculated on a basis of about 0.2 mg/day to about 50 mg/day, or 0.5 mg/day to about 50 mg/day, or of about 1 mg/day to about 10 mg/day, or about 2 mg/day to about 5 mg/day, e.g. about 3 mg/day. To calculate a weekly dose, these amounts should be multiplied by 7, and for a monthly dose these amounts should be multiplied by 30. Doses for other dosing regimens can readily be calculated by multiplying the daily dose with the number of days between each administration. For therapy, the dose should be somewhat higher and should be calculated on a basis of about 1 mg/day to about 150 mg/day, or of about 2 mg/day to about 100 mg/day, or of about 5 mg/day to about 50 mg/day, or about 10 mg/day to about 25 mg/day, e.g. about 15 mg/day. The corresponding weekly or monthly doses can be calculated as set forth above. For applications in prevention, the same dosing as for therapeutic applications may be used.

In one embodiment, the micro- or nanoparticles in the compositions of the invention mainly comprise polymorph I of TMC278 and the surface modifier, the combined amount of which may at least comprise about 50%, or at least about 80%, or at least about 90%, or at least about 95%, or at least about 99% of the micro- or nanoparticles.

The micro- or nanoparticles of the present invention have a surface modifier adsorbed on their surface, acting as a wetting agent as well as a stabilizer of the suspension.

Suitable surface modifiers can be selected from various excipients such as gelatin, casein, lecithin, salts of negatively charged phospholipids or the acid form thereof (such as phosphatidyl glycerol, phosphatidyl inosite, phosphatidyl serine, phosphatic acid, and their salts such as alkali metal salts, e.g. their sodium salts, for example egg phosphatidyl glycerol sodium, such as the product available under the tradename Lipoid™), gum acacia, stearic acid, benzalkonium chloride, polyoxyethylene alkyl ethers, e.g., macrogol ethers such as cetomacrogol 1000, polyoxyethylene castor oil derivatives; polyoxyethylene stearates, colloidal silicon dioxide, sodium dodecylsulfate, carboxymethylcellulose sodium, bile salts such as sodium taurocholate, sodium desoxytaurocholate, sodium desoxycholate; methylcellulose, hydroxyethyl-cellulose, hydroxypropylcellulose, hydroxypropylmethylcellulose, magnesium aluminate silicate, polyvinyl alcohol (PVA), poloxamers, such as Pluronic™ F68, F108 and F127 which are block copolymers of ethylene oxide and propylene oxide; tyloxapol; Vitamin E-TGPS (α-tocopheryl polyethylene glycol succinate, in particular α-tocopheryl polyethylene glycol 1000 succinate); poloxamines, such as Tetronic™ 908 (T908), which is a tetrafunctional block copolymer derived from sequential addition of ethylene oxide and propylene oxide to ethylenediamine; dextran; lecithin; dioctyl ester of sodium sulfosuccinic acid such as the products sold under the tradename Aerosol OT™ (AOT); sodium lauryl sulfate (Duponol™ P); alkyl aryl polyether sulfonate available under the tradename Triton™ X-200; polyoxyethylene sorbitan fatty acid esters (Tweens™ 20, 40, 60 and 80); sorbitan esters of fatty acids (Span™ 20, 40, 60 and 80 or Arlacel™ 20, 40, 60 and 80); polyethylene glycols (such as those sold under the tradename Carbowax™ 3550 and 934); sucrose stearate and sucrose distearate mixtures such as the product available under the tradename Crodesta™ F110 or Crodesta™ SL-40; hexyldecyl trimethyl ammonium chloride (CTAC); polyvinylpyrrolidone (PVP). If desired, two or more surface modifiers can be used in combination.

Particular surface modifiers are selected from poloxamers, α-tocopheryl polyethylene glycol succinates, polyoxyethylene sorbitan fatty acid esters, and salts of negatively charged phospholipids or the acid form thereof. More in particular the surface modifiers are selected from Pluronic™ F108, Vitamin E TGPS, Tween™ 80, and Lipoid™ EPG. One or more of these surface modifiers may be used. Pluronic™ F108 corresponds to poloxamer 338 and is the polyoxyethylene/polyoxypropylene block copolymer that conforms generally to the formula $HO-[CH_2CH_2O]_x-[CH(CH_3)CH_2O]_y-[CH_2CH_2O]_z-H$ in which the average values of x, y and z are respectively 128, 54 and 128. Other commercial names of poloxamer 338 are Hodag Nonionic™ 1108-F and Synperonic™ PE/F108. In one embodiment, the surface modifier comprises a combination of a polyoxyethylene sorbitan fatty acid ester and a phosphatidyl glycerol salt (in particular egg phosphatidyl glycerol sodium).

The relative amount (w/w) of polymorph I of TMC278 to the surface modifier may vary but can be in the range of 1:2 to about 20:1, in particular in the range of 1:1 to about 10:1, e.g. about 4:1.

The micro- or nanoparticles of polymorph I of TMC278 can be prepared by means of particle size reduction (nanonization) by mechanical means. The polymorph I of TMC278, preferably in micronized form, is brought in an aqueous dispersion medium in the presence of a surface modifier and grinding media are applied to reduce the particle size to the desired effective particle size. A general procedure for preparing the particles of this invention comprises
(a) obtaining polymorph I of TMC278 in micronized form;
(b) adding the micronized TMC278 to a liquid medium to form a premix/predispersion; and
(c) subjecting the premix to mechanical means in the presence of a grinding medium to reduce the average effective particle size.

Polymorph I of TMC278 in micronized form is prepared using techniques known in the art. The average effective particle size of the TMC278 active agent in the predispersion may be less than about 100 µm as determined by sieve analysis. Where the average effective particle size is greater than about 100 µm, it preferably is reduced to less than about 100 µm. The micronized polymorph I of TMC278 can then be added to an aqueous medium to form a predispersion.

The mechanical means applied to reduce the effective average particle size of polymorph I of TMC278 comprises a roller mill or similar means, using beads such as $ZrO_2$ beads. The size reduction takes place at a temperature that does not significantly degrade the TMC278 compound, preferably less than 30 to 40° C., e.g. at ambient temperature, if needed using cooling.

The micro- or nanoparticle compositions according to the present invention contain an aqueous carrier that is pharmaceutically acceptable, e.g. sterile water optionally in admixture with other pharmaceutically acceptable ingredients such as suspending agents, buffers, pH adjusting agents, preservatives, isotonizing agents.

Suitable buffering agents and pH adjusting agents should be used in amount sufficient to render the dispersion neutral to very slightly basic (up to pH 8.5), preferably in the pH range of 7 to 7.5. Particular buffers are the salts of week acids. Buffering and pH adjusting agents that can be added may be selected from tartaric acid, maleic acid, glycine, sodium lactate/lactic acid, ascorbic acid, sodium citrates/citric acid, sodium acetate/acetic acid, sodium bicarbonate/carbonic acid, sodium succinate/succinic acid, sodium benzoate/benzoic acid, sodium phosphates, tris(hydroxymethyl)aminomethane, sodium bicarbonate/sodium carbonate, ammonium hydroxide, benzene sulfonic acid, benzoate sodium/acid, diethanolamine, glucono delta lactone, hydrochloric acid, hydrogen bromide, lysine, methanesulfonic acid, monoethanolamine, sodium hydroxide, tromethamine, gluconic acid, glyceric acid, gluratic acid, glutamic acid, ethylene diamine tetraacetic acid (EDTA), triethanolamine, including mixtures thereof.

Preservatives comprise antimicrobials and anti-oxidants which can be selected from the group consisting of benzoic acid, benzyl alcohol, butylated hydroxyanisole (BHA), butylated hydroxytoluene (BHT), chlorbutol, a gallate, a hydroxybenzoate, EDTA, phenol, chlorocresol, metacresol, benzethonium chloride, myristyl-γ-piccolinium chloride, phenylmercuric acetate and thimerosal. Radical scavengers include BHA, BHT, Vitamin E and ascorbyl palmitate, and mixtures thereof. Oxygen scavengers include sodium ascorbate, sodium sulfite, L-cysteine, acetylcysteine, methionine, thioglycerol, acetone sodium bisulfite, isoascorbic acid, hydroxypropyl cyclodextrin. Chelating agents include sodium citrate, sodium EDTA and malic acid.

An isotonizing agent or isotonifier may be present to ensure isotonicity of the micro- or nanoparticle compositions of the invention, and includes sugars such as glucose, dextrose, sucrose, fructose, trehalose, lactose; polyhydric sugar alcohols, preferably trihydric or higher sugar alcohols, such as glycerin, erythritol, arabitol, xylitol, sorbitol and mannitol. Alternatively, sodium chloride, sodium sulfate, or other appropriate inorganic salts may be used to render the solutions isotonic. These isotonifiers can be used alone or in combination. The suspensions conveniently comprise from 0 to 10% (w/v), in particular 0 to 6% of isotonizing agent. Of interest are nonionic isotonifiers, e.g. glucose, as electrolytes may affect colloidal stability.

The viscosity of the micro- or nanoparticle compositions of polymorph I of TMC278 should be sufficiently low to allow administration by injection, below about 75 mPa·s, or below 60 mPa·s.

Preferably, the micro- or nanoparticle compositions of the invention comprise as much polymorph I of TMC278 as can be tolerated so as to keep the injected volume to a minimum, in particular from 3 to 40% (w/v), or from 3 to 30% (w/v), or from 3 to 20% (w/v), or from 10 to 30% (w/v), of polymorph I of TMC278. In one embodiment the micro- or nanoparticle compositions contain about 10%, or about 20%, or about 30% (w/v) of polymorph I of TMC278.

In one embodiment, the aqueous suspensions may comprise by weight, based on the total volume of the composition:
(a) from 3% to 50% (w/v), or from 10% to 40% (w/v), or from 10% to 30% (w/v), of polymorph I of TMC278;
(b) from 0.5% to 10%, or from 0.5% to 2% (w/v) of a wetting agent;
(c) from 0% to 10%, or from 0% to 5%, or from 0% to 2%, or from 0% to 1% of one or more buffering agents;
(d) from 0% to 10%, or from 0% to 6% (w/v) of a isotonizing agent
(e) from 0% to 2% (w/v) preservatives; and
(f) water for injection q.s. ad 100%.

To the suspensions may optionally be added an amount of acid or base to bring the pH to a value of about pH 7. Suitable acids or bases are any of those that are physiologically acceptable, e.g. HCl, HBr, sulfuric acid, alkali metal hydroxides such as NaOH.

The administration of polymorph I of TMC278 as in the present invention may suffice to treat HIV infection although in a number of cases it may be recommendable to co-administer other HIV inhibitors, such as HIV inhibitors of other classes, in particular those selected from NRTIs, PIs, fusion inhibitors, integrase inhibitors, and CCR5-inhibitors.

In certain instances, the treatment of HIV infection may be limited to only the administration of a micro- or nanoparticle composition of polymorph I of TMC278, i.e. as monotherapy without co-administration of further HIV inhibitors. This option may be recommended, for example, where the viral load is relatively low, for example where the viral load is below about 200 copies/ml, in particular below about 100 copies/ml, more in particular below 50 copies/ml, specifically below the detection limit of the virus. In one embodiment, this type of monotherapy, which can be referred to as maintenance therapy, is applied after initial treatment with a combination of HIV drugs, in particular with any of the HAART combinations during a certain period of time until the viral load in blood plasma reaches the afore mentioned low viral level.

In a further aspect the present invention relates to the use of a micro- or nanoparticle composition comprising an antivirally effective amount Polymorph I of TMC278, for the manufacture of a medicament for maintenance therapy of a subject being infected with HIV, wherein the composition is administered or is to be administered intermittently at a time interval that is in the range of one week to one year, or one week to two years, or one month to three months, or any of the other time intervals mentioned herein.

This invention also provides a method for the long term treatment of a patient infected with HIV, said method comprising
(a) the treatment of said patient with a combination of HIV inhibitors; followed by
(b) the intermittent administration of a micro- or nanoparticle composition comprising an anti-virally effective amount polymorph I of TMC278, as specified herein, wherein the composition is administered at a time interval ranging from one week to one year, or one month to three months, or any of the other time intervals mentioned herein.

The present invention also concerns a micro- or nanoparticle composition as described herein for use as a medicament in the treatment or prophylaxis of HIV infection, and the use of a micro- or nanoparticle composition as described herein for the manufacture of a medicament for the prophylaxis or treatment of HIV infection. The invention further concerns a method of treating a subject infected with HIV, said method comprising the administration of a therapeutically effective amount of a micro- or nanoparticle composition as described herein.

The polymorph I of TMC278 can be used alone or in combination with other antiviral, in particular anti-retroviral agents. Thus, the present invention also relates to a product containing (a) polymorph I of TMC278, and (b) one or more other antiretroviral compounds, as a combined preparation for simultaneous, separate or sequential use in anti-HIV treatment. The different agents may be combined in a single preparation together with pharmaceutically acceptable carriers. Thus, the present invention also relates to a pharmaceutical composition comprising a pharmaceutically acceptable carrier and (a) a therapeutically effective amount of a polymorph I of TMC278 and (b) one or more other antiretroviral agents.

Said other antiretroviral compounds comprise any antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126, 443), AVX 754 ((−)-dOTC), fozivudine tidoxil (FZT), phosphazide, HDP-990003, KP-1461, MIV-210, racivir (PSI-5004), UC-781 and the like; non-nucleoside reverse transcriptase inhibitors (NNRTIs) such as delavirdine (DLV), efavirenz (EFV), nevirapine (NVP), dapivirine (TMC120), etravirine (TMC125), DPC-082, (+)-Calanolide A, BILR-355, and the like; nucleotide reverse transcriptase inhibitors (NtRTIs), e.g. tenofovir ((R)-PMPA) and tenofovir disoproxil fumarate (TDF), and the like; nucleotide-competing reverse transcriptase inhibitors (NcRTIs), e.g. the compounds of WO 2004/046143; inhibitors of trans-activating proteins, such as TAT-inhibitors, e.g. RO-5-3335, BI-201, and the like; REV inhibitors; protease inhibitors e.g. ritonavir (RTV), saquinavir (SQV), lopinavir (ABT-378 or LPV), indinavir (IDV), amprenavir (APV or VX-478), TMC126, nelfinavir (NFV or AG-1343), atazanavir (BMS 232, 632), darunavir (TMC114), fosamprenavir (GW433908 or VX-175), brecanavir (GW-640385, VX-385), P-1946, PL-337, PL-100, tipranavir (TPV or PNU-140690), AG-1859, AG-1776, Ro-0334649 and the like; entry inhibitors, which comprise fusion inhibitors (e.g. enfuvirtide (T-20)), attachment inhibitors and co-receptor inhibitors, the latter comprise the CCR5 antagonists (e.g: ancriviroc, CCR5 mAb004, maraviroc (UK-427, 857), PRO-140, TAK-220, TAK-652, vicriviroc (SCH-D, SCH-417, 690)) and CXR4 antagonists (e.g. AMD-070, KRH-27315), examples of entry inhibitors are PRO-542, TNX-355, BMS-488, 043, BlockAide/CR™, FP 21399, hNM01, nonakine, VGV-1; a maturation inhibitor for example is PA-457; inhibitors of the viral integrase e.g. raltegravir (MK-0518), elvitegravir (JTK-303 or GS-9137), BMS-538, 158; ribozymes; immunomodulators; monoclonal antibodies; gene therapy; vaccines; siRNAs; antisense RNAs; microbicides; Zinc-finger inhibitors.

As used herein, the word "substantially" does not exclude "completely" e.g. a composition which is "substantially free" from Y may be completely free from Y. Where necessary, the word "substantially" may be omitted from the definition of the invention. The term "about" in connection with a numerical value is meant to have its usual meaning in the context of the numerical value. Where necessary the word "about" may be replaced by the numerical value ±10%, or ±5%, or ±2%, or ±1%. All refereces cited herein are incorporated by reference in their entirety.

EXAMPLES

Example 1

Preparation of Polymorph I of TMC278

Polymorph I of TMC278 was prepared by dissolving about 4.2 g of TMC278 in 500 ml 2-propanone while stirring and heating the solution up to reflux temperature until obtaining a clear solution. After filtering this clear solution it was cooled below 0° C. on a bath of ethanol and dry ice (solid $CO_2$). The solvent was evaporated until a precipitate was obtained. The obtained crystals were dried overnight under vacuum at room temperature.

Example 2

Infrared (IR) Spectrometry KBr Dispersion

| Polymorph I of TMC278 was mixed with alkali halide and pressed to a pellet. | |
|---|---|
| apparatus: | Nicolet Magna 560 ™ Fourier Transform IR (FTIR) spectrophotometer |
| number of scans: | 32 |
| resolution: | 1 cm$^{-1}$ |
| wavelength range: | 4000 to 400 cm$^{-1}$ |
| baseline correction: | yes |
| detector: | DTGS with KBr windows |
| beamsplitter: | Ge on KBr |
| alkali halide: | KBr |

Figure 1:
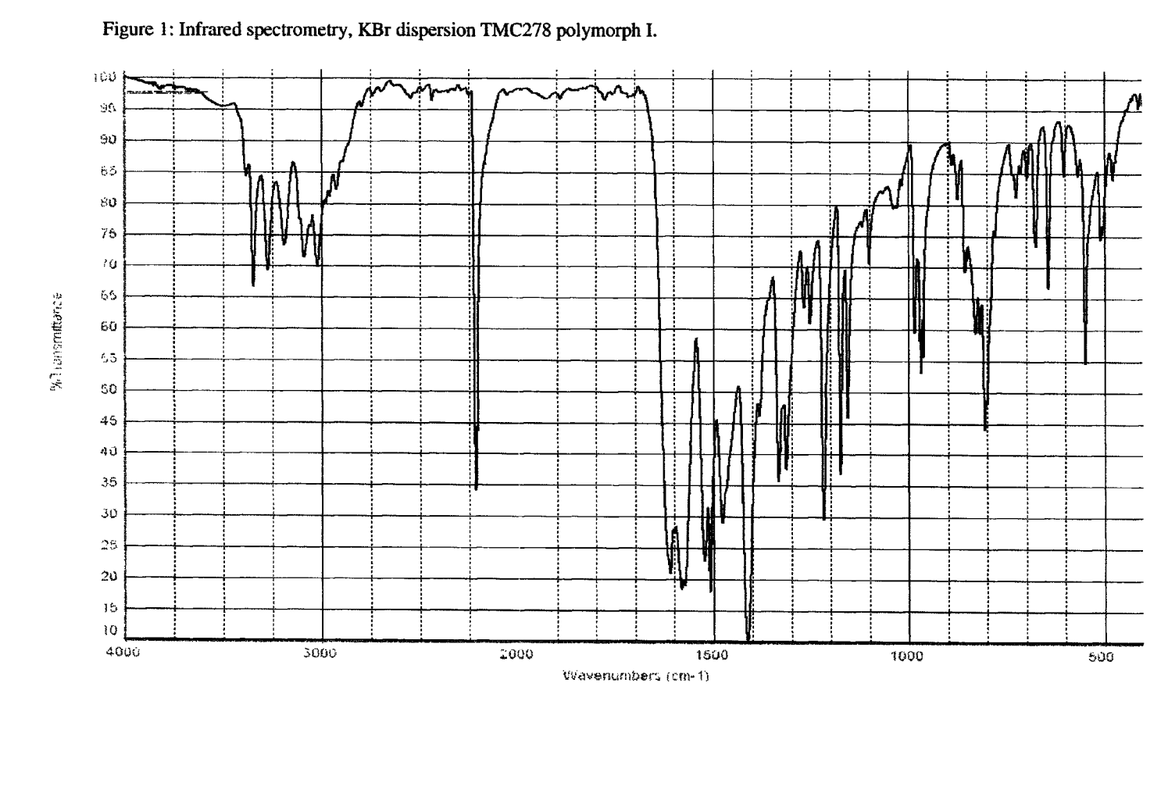
FIG. 1: Infrared spectrometry, KBr dispersion TMC278 polymorph I.

TMC278 polymorph I was characterized by an FTIR spectrum with typical absorption bands at about 3348, 3274, 2217, 2209, 1477 and 1334 cm$^{-1}$. Additional absorption bands were observed at 3190, 1611, 1523, 1509, 1102, 970, 963, 829 and 820 cm$^{-1}$. See FIG. 1.

Figure 5:
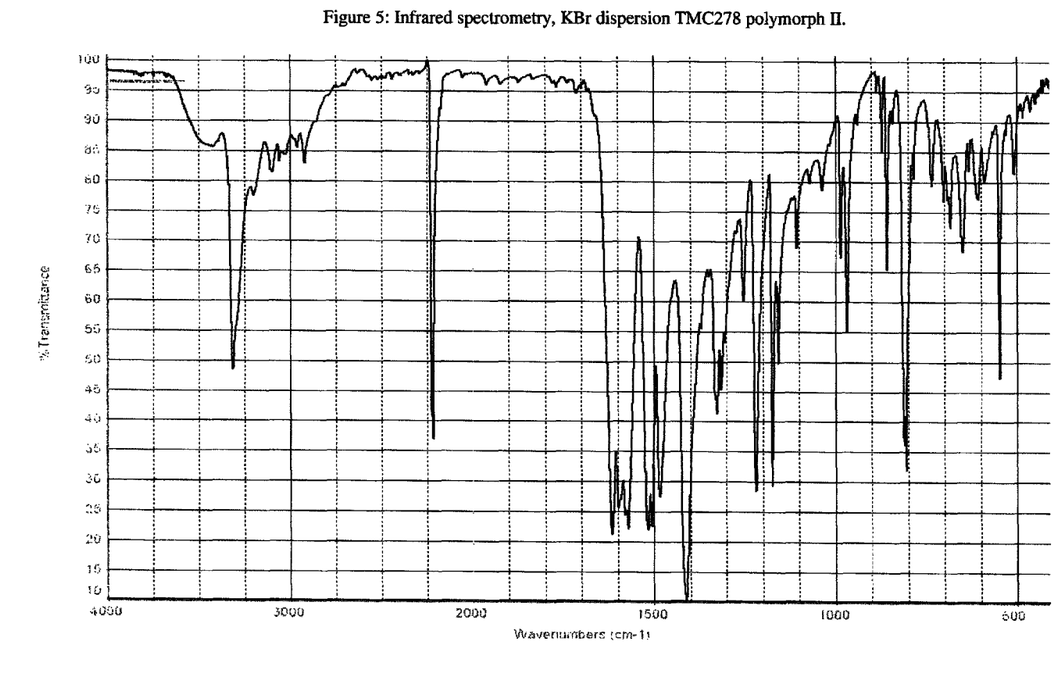
FIG. 5: Infrared spectrometry, KBr dispersion TMC278 polymorph II

TMC278 polymorph II was characterized by an FTIR spectrum with typical absorption bands at about 3316, 2223, 2215, 1483, and 1325 cm$^{-1}$. Additional absorption bands are observed at 3201, 1617, 1516, 1505, 1303, 1106, and 967 cm$^{-1}$. See FIG. 5.

All above mentioned values for the absorption bands are ±2 cm$^{-1}$.

Example 3

Powder XRD

X-ray powder diffraction (XRPD) analyses were carried out on a Philips X'PertPRO MPD diffractometer PW3050/60 with generator PW3040. The instrument was equipped with a Cu LFF X-ray tube PW3373/00. Polymorph I of TMC278 was spread on a zero background sample holder.

The instrument parameters were the following:

| | |
|---|---|
| generator voltage: | 45 kV |
| generator amperage: | 40 mA |
| geometry: | Bragg-Brentano |
| stage: | spinner stage |

The measurement conditions were the following:

| | |
|---|---|
| scan mode: | continuous |
| scan range: | 3 to 50° 2θ |
| step size: | 0.01675°/step |
| counting time: | 60.59 sec/step |
| spinner revolution time: | 1 sec |
| radiation type: | CuKα |
| radiation wavelength: | 1.54056 Å |

| Incident beam path | | Diffracted beam path | |
|---|---|---|---|
| program. divergence slit: | 15 mm | long anti scatter shield: | + |
| Soller slit: | 0.04 rad | Soller slit: | 0.04 rad |
| beam mask: | 15 mm | Ni filter: | + |
| anti scatter slit: | 1° | detector: | X'Celerator |
| beam knife: | + | | |

Figure 2:
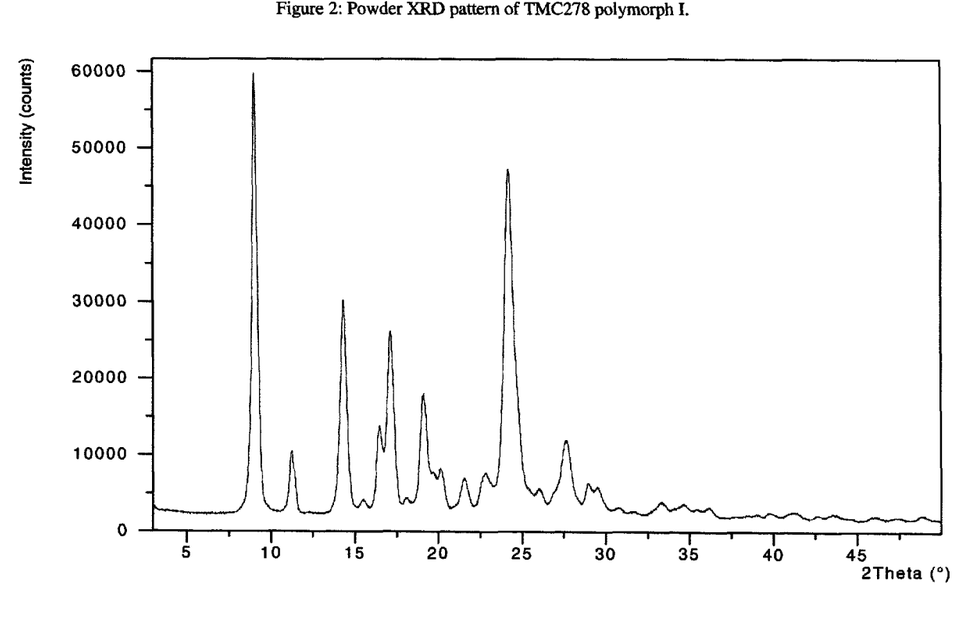
FIG. 2: Powder X-ray diffraction (XRD) pattern of TMC278 polymorph I.

TMC278 polymorph I was characterized by main diffraction peaks at two-theta positions 9.0°±0.2°, 14.3°±0.2°, 17.1°±0.2° and 24.2°±0.2°. TMC278 polymorph I was further characterized by X-ray powder diffraction peaks at two-theta positions 11.3°±0.2°, 19.1°±0.2°, and 27.6°±0.2°. See FIG. 2.

Figure 6:
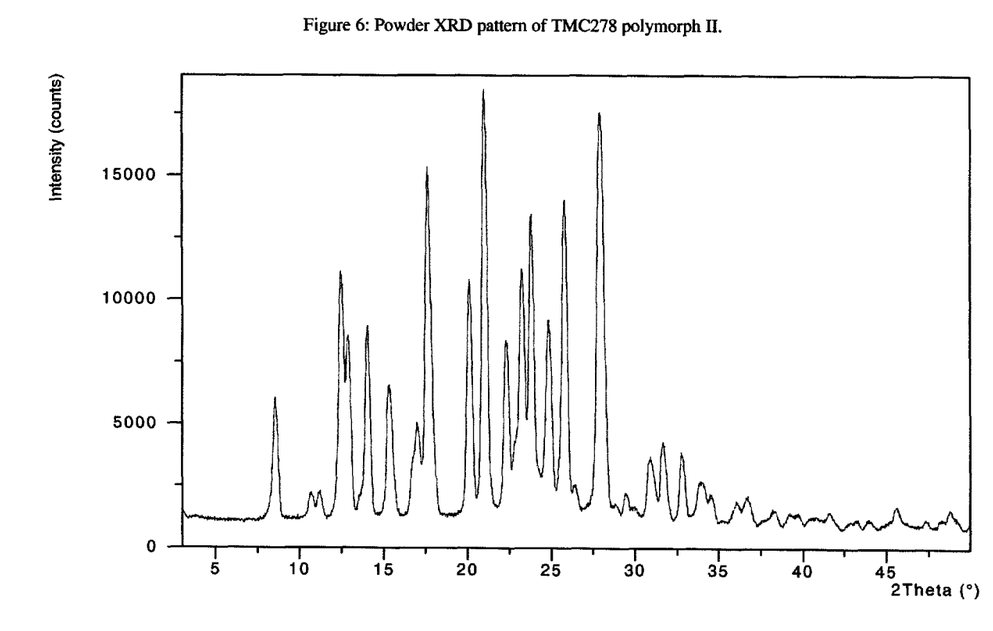
FIG. 6: Powder XRD pattern of TMC278 polymorph II.

TMC278 polymorph II was characterized by main diffraction peaks at two-theta positions 17.6°±0.2°, 1.0°±0.2°, 25.8°±0.2° and 27.9°±0.2°. TMC278 polymorph II was further characterized by X-ray powder diffraction peaks at two-theta positions 8.5°±0.2°, 12.4°±0.2°, 12.9°±0.2° and 24.8°±0.2°. See FIG. 6.

The peaks in the XRD spectra can show intensity variations due to a number of reasons, most importantly due to the processing history of the sample.

Example 4

Differential Scanning Calorimetry (DSC)

About 3 mg of Polymorph I of TMC278 was transferred into a standard aluminum TA-Instruments sample pan. The sample pan was closed with the appropriate cover and the DSC curve was recorded on a TA-Instruments Q1000 MTDSC equipped with a RCS cooling unit. The following parameters were used:

| | |
|---|---|
| initial temperature: | 25° C. |
| heating rate: | 10° C./min |
| final temperature: | 280° C. |
| nitrogen flow: | 30 ml/min |

Figure 3:
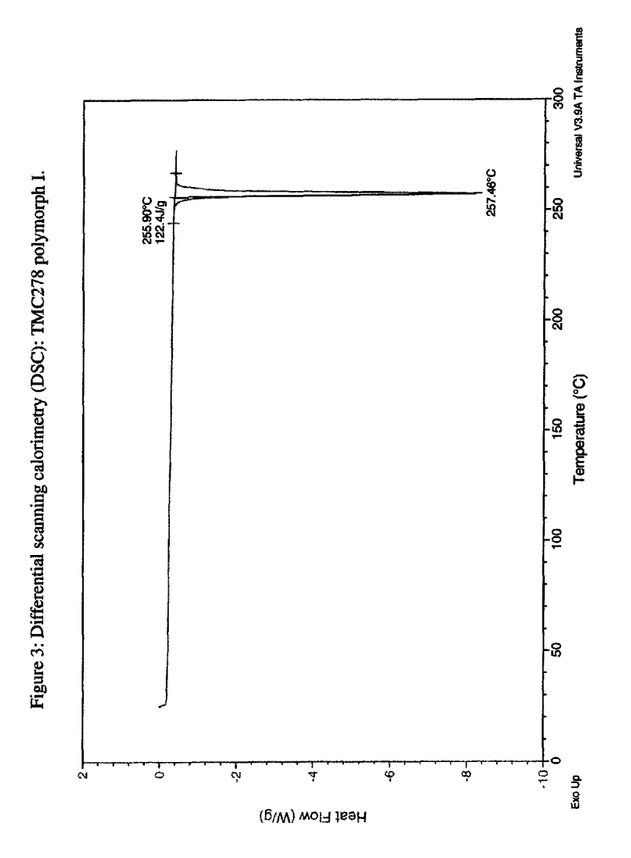
FIG. 3: Differential scanning calorimetry (DSC): TMC278 polymorph I.

The melting of TMC278 polymorph I occurred at 257.5° C. (peak maximum) with a heat of fusion of 122 J/g. See FIG. 3.

Figure 7:
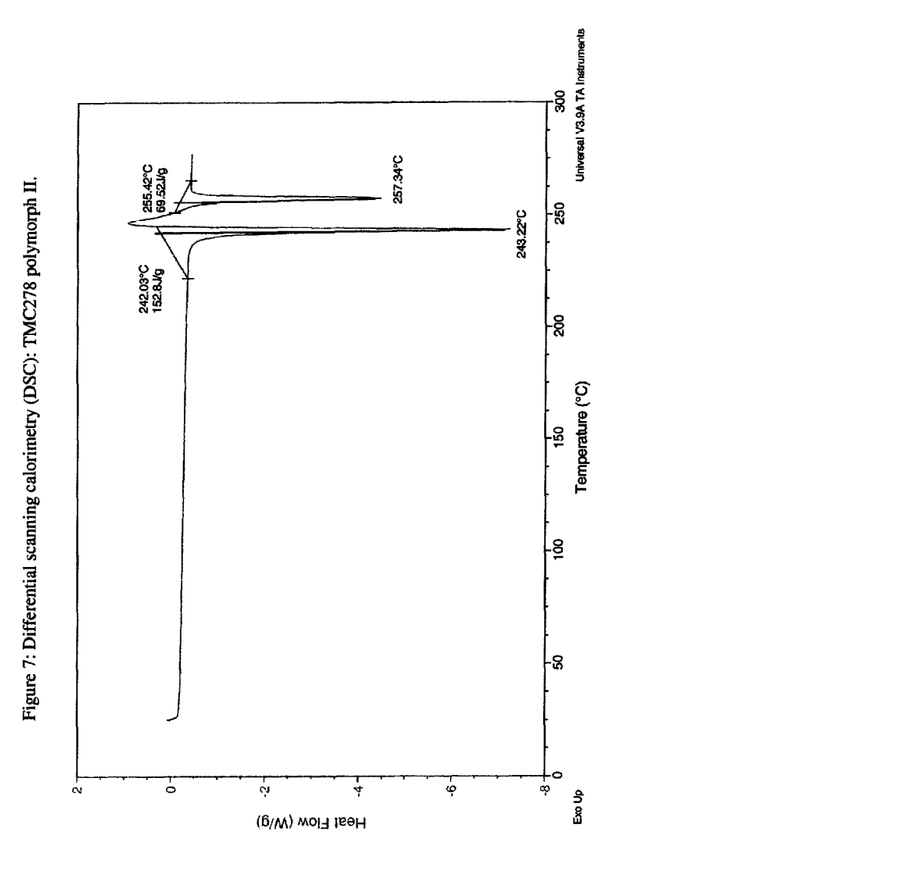
FIG. 7: DSC: TMC278 polymorph II.

The melting of TMC278 polymorph II occurred at 243.2° C. (peak maximum) with a heat of fusion of 153 J/g followed by a polymorphic conversion of polymorph II into polymorph I. Due to the occurring conversion, DSC was not suitable for the determination of the polymorphic composition of TMC278. See FIG. 7.

Example 5

Intrinsic Dissolution

A Hanson Research SR6™ dissolution testing station equipped with a USP dissolution apparatus 2 as paddle and a poly(tetrafluoroethylene (PTFE) tablet holder was used. UV spectrometry was used to determine the concentration of TMC278 in solution. The UV analysis was carried out on an Agilent 8453™ spectrophotometer using a 2 ml cuvet. A single wavelength measurement at 266 nm was recorded with single component analysis (SCA), a single component measurement.

Tabletting

About 125 mg of the compound was weighed into a mould with a diameter of 0.8 cm. A tablet was made with a Speca press imposing a pressure of 1 ton for tabletting. The surface area of the tablet was 0.5026 cm$^2$. The tablet was adhered to the PTFE tablet holder.

Reference Solution for UV Analysis 21.8 mg of TMC278 was weighed into a volumetric flask of 25 ml. The product was dissolved in a 1:1.5 tetrahydrofuran/methanol mixture. A 1 ml aliquot was transferred into a 200 ml volumetric flask and diluted to the mark using 0.01N HCl. The concentration of the reference solution was 0.4364 mg/ml.

Dissolution

The tablet holders with the tablets were placed in a USP2 dissolution bath. The vessels contained 500 ml 0.01N HCl/methanol 1:1 and were thermostatically controlled at 37° C. The paddles were used with a rotation speed of 150 rpm (rounds per minute). A sample was withdrawn each 10 minutes and the concentration was determined with UV spectrometry. The slope was calculated on the measuring points between 0 and 60 minutes. The slope was expressed as mg %/minute. The intrinsic dissolution rate (IDR), expressed as mg/(cm$^2$×min), was calculated.

Intrinsic Dissolution

Figure 4:
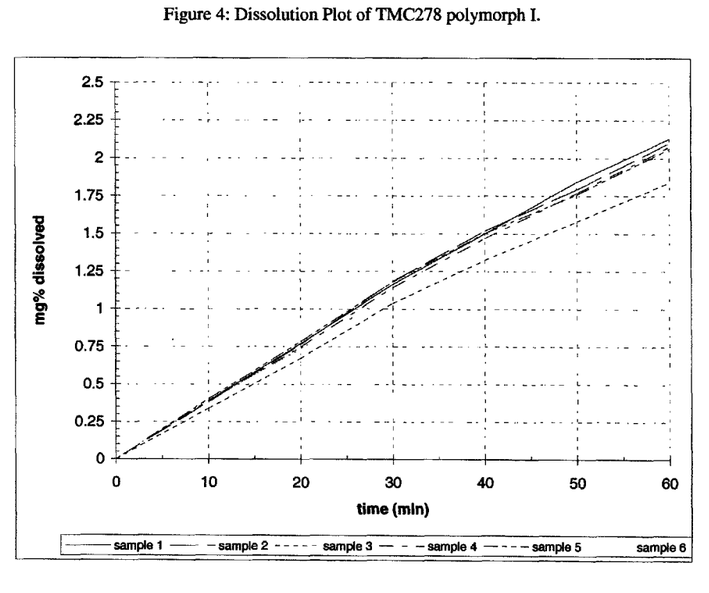
FIG. 4: Dissolution Plot of TMC278 polymorph I.

The average intrinsic dissolution rate of TMC278 polymorph I was 0.3362. The dissolution plots of TMC278 polymorph I are presented in FIG. 4.

| | TMC278 polymorph I | |
|---|---|---|
| | slope | mg/(cm$^2$ × min) |
| Sample 1 | 0.0358 | 0.3559 |
| Sample 2 | 0.0353 | 0.3508 |
| Sample 3 | 0.0309 | 0.3074 |
| Sample 4 | 0.0347 | 0.3447 |
| Sample 5 | 0.0343 | 0.3417 |
| Sample 6 | 0.0319 | 0.3169 |
| average | 0.0338 | 0.3362 |

The slope was calculated from 0 to 60 min.

Figure 8:
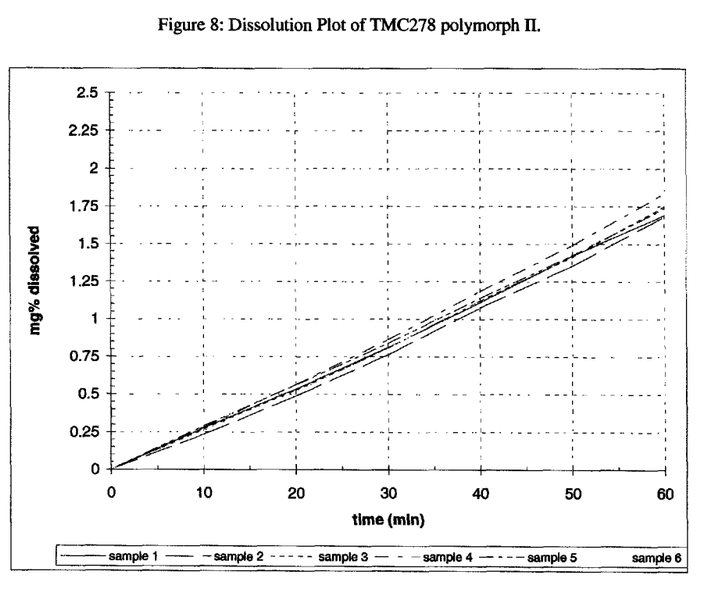
FIG. 8: Dissolution Plot of TMC278 polymorph II.

The average intrinsic dissolution rate of polymorph II was 0.2886. The dissolution plots of TMC278 polymorph II are presented in FIG. 8.

| | TMC278 polymorph II | |
|---|---|---|
| | slope | mg/(cm$^2$ × min) |
| Sample 1 | 0.0283 | 0.2819 |
| Sample 2 | 0.0281 | 0.2795 |
| Sample 3 | 0.0290 | 0.2886 |
| Sample 4 | 0.0305 | 0.3035 |
| Sample 5 | 0.0288 | 0.2861 |
| Sample 6 | 0.0294 | 0.2921 |
| average | 0.0290 | 0.2886 |

The slope was calculated from 0 to 60 min.

Solubility

The following table shows the solubility of TMC278 polymorph I in buffer pH4, buffer pH2 and 0.01N HCl.

| | TMC278 polymorph I | |
|---|---|---|
| Medium | Solubility mg/100 ml | pH |
| Buffer pH4 | 0.07 | 4.0 |
| Buffer pH2 | 0.64 | 2.1 |
| 0.01N HCl | 4.1 | 2.1 |

The solubility of TMC278 polymorph II in buffer pH4, buffer pH2 and 0.01N HCl is presented in the following table.

| | TMC278 polymorph II | |
|---|---|---|
| Medium | Solubility mg/100 ml | pH |
| Buffer pH4 | 0.03 | 4.0 |
| Buffer pH2 | 0.64 | 2.1 |
| 0.01N HCl | 1.9 | 2.1 |

Example 6

Preparation of Nanosuspension of Polymorph I of TMC278

Glass bottles of 250 ml and ZrO$_2$ beads, used as the milling media, are sterilized in an autoclave. Five grams of drug substance are put into a 250 ml glass bottle together with a solution of 1.25 g Pluronic F108 in 60 ml of water for injection. 300 g of ZrO$_2$-beads with an average particle size of 500 µm are added and the bottle is placed on a roller mill. The suspension is micronized at 100 rpm during 72 h. At the end of the milling process, the concentrated nanosuspension is removed with a syringe and filled into vials. The resulting formulation is Formula I in the following table. Determination of the concentration is done by HPLC/UV. A dilution is made to a final concentration of 25 mg/ml of TMC278. The resulting suspension is shielded from light.

Using similar procedures, Formulations 2, 3 and 4 are prepared. These are titrated with sodium hydroxide 1N solution to a pH of about 7. In formulations 2, 3 and 4 the Lipoid™ EPG is solubilized in the Tween™ 80.

| Ingredient | Formula 1 | Formula 2 | Formula 3 | Formula 4 |
|---|---|---|---|---|
| Polymorph I of TMC278 | 5 g | 300 mg | 300 mg | 300 mg |
| Pluronic ™ F108 | 1.25 g | — | — | — |
| Tween ™ 80 | — | 75 mg | 75 mg | 75 mg |
| Lipoid ™ EPG | — | 9.375 mg | 9.375 mg | 9.375 mg |
| Glucose | — | 50 mg | 50 mg | 50 mg |
| NaH$_2$PO$_4$.1aq | — | — | 2 mg | 2 mg |
| citric acid.1aq | — | — | — | 1 mg |
| NaOH 1 N | — | at pH 6.72 | at pH 6.98 | at pH 6.99 |

The following study compares the plasma kinetics of TMC278 after single intramuscular (IM) or subcutaneous injection of a nanosuspension (Formula I, see above) at 5 mg/kg in male beagle dogs.

Four healthy male beagle dogs with body weights ranging from 8 to 16 kg at the start of the study, are used. Dogs are identified by an ear tattoo number. Two dogs are dosed intramuscularly (IM) in the left and right musculus biceps femoris. Two dogs are dosed subcutaneously (SC) in the left and right thoracal region. The injection volume is 2xx 0.1 ml/kg in all treatment groups. A 20 G needle is used.

Blood samples of 3 ml are taken from the left jugular vein from all dogs on day 0 at 0 h (predose), 20 min, 1 h, 3 h, 8 h and 24 h post-dose and further on days 2, 3, 6, 8, 10, 13, 16, 20, 23, 27, 29, 36, 43, 50, 57, 64, 71, 78, 85 and 92 at approximately 8 AM. Blood samples are placed on EDTA (EDTA Vacuette Greiner, Cat. No. 454086, Greiner Labortechnik N.V.). Within 2 h of blood sampling, samples are centrifuged at room temperature at about 1900×g for 10 minutes to allow plasma separation, and plasma is immediately transferred into a second tube and stored in the freezer within 2 h after the start of centrifugation. Plasma samples are analysed individually for TMC278 by means of a validated LC-MS/MS-method.

The invention claimed is:
1. Polymorph I of (E) 4-[[4-[[4-(2-cyanoethenyl)-2,6-dimethylphenyl]amino]-2-pyrimidinyl]amino]benzonitrile.
2. The polymorph of claim 1 characterized by X-ray powder diffraction peaks at two-theta positions 9.0°±0.2°, 14.3°±0.2°, 17.1°±0.2° and 24.2°±0.2°.

3. The polymorph of claim 2 further characterized by X-ray powder diffraction peaks at two-theta positions 11.3°±0.2°, 19.1°±0.2°, and 27.6°±0.2°.

4. A process for preparing the polymorph of claim 1, wherein the said polymorph is prepared by dissolving TMC278 in a ketone and heating the solution to reflux temperature, and allowing this solution to cool.

5. A solid pharmaceutical composition comprising as active ingredient polymorph I of TMC278 and a pharmaceutically acceptable carrier.

6. A process for preparing the polymorph of claim 2, wherein the said polymorph is prepared by dissolving TMC278 in a ketone and heating the solution to reflux temperature, and allowing this solution to cool.

7. A process for preparing the polymorph of claim 3, wherein the said polymorph is prepared by dissolving TMC278 in a ketone and heating the solution to reflux temperature, and allowing this solution to cool.

8. A micro- or nanoparticle pharmaceutical composition for administration by intramuscular or subcutaneous injection, comprising a therapeutically effective amount of polymorph I of TMC278, comprising polymorph I of TMC278, in micro- or nanoparticle form, having a surface modifier adsorbed to the surface thereof, suspended in a pharmaceutically acceptable aqueous carrier.

9. A pharmaceutical composition comprising a micro- or nanoparticle composition as defined in claim 8.

10. A method of treating in a subject HIV infection comprising administering to the subject a therapeutically effective amount of a pharmaceutical composition of claim 9.

11. The method of claim 10, wherein the composition is administered or is to be administered intermittently at a time interval that is in the range of one week to one year, or one week to two years.

12. The method of claim 10, wherein the composition is administered or is to be administered at a time interval that is in the range of one week to one month, or in the range of one month to three months, or in the range of three months to six months.

* * * * *

UNITED STATES PATENT AND TRADEMARK OFFICE
CERTIFICATE OF CORRECTION

PATENT NO.       : 8,426,434 B2
APPLICATION NO.  : 12/668079
DATED            : April 23, 2013
INVENTOR(S)      : Stokbroekx et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this
Eighth Day of September, 2015

Michelle K. Lee
*Director of the United States Patent and Trademark Office*